US012622656B2

(12) United States Patent
Burbar et al.

(10) Patent No.: US 12,622,656 B2
(45) Date of Patent: May 12, 2026

(54) METHODS AND APPARATUS FOR MEDICAL IMAGING EVENT DETECTION AND IMAGE RECONSTRUCTION

(71) Applicant: Siemens Medical Solutions USA, Inc., Malvern, PA (US)

(72) Inventors: Ziad Burbar, Knoxville, TN (US); Stefan Siegel, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 257 days.

(21) Appl. No.: 18/615,044

(22) Filed: Mar. 25, 2024

(65) Prior Publication Data

US 2025/0295368 A1    Sep. 25, 2025

(51) Int. Cl.
 *A61B 6/03*        (2006.01)
 *G01T 1/29*        (2006.01)
(52) U.S. Cl.
 CPC ............ *A61B 6/037* (2013.01); *G01T 1/2985* (2013.01)
(58) Field of Classification Search
 CPC ........ G01T 1/2985; G06T 12/30; A61B 6/037
 See application file for complete search history.

(56) References Cited

U.S. PATENT DOCUMENTS

2025/0299387 A1*   9/2025  Burbar .................. A61B 6/037

FOREIGN PATENT DOCUMENTS

WO      WO-2012171059 A1 * 12/2012   ............. G06F 17/18

* cited by examiner

*Primary Examiner* — Casey Bryant

(57)            ABSTRACT

Systems and methods for detecting multiple events during nuclear imaging scans, and for reconstructing images based on the detected events, are disclosed. In some embodiments, an image scanning system scans a subject, and generates a signal characterizing a detection event. The system applies a peak detection process to the signal and, based on the application of the peak detection process, detects a position of each of a plurality of peaks of the signal. Further, the system determines an amplitude of each of the peaks of the signal. The system also determines an energy value for each of the peaks based on applying a curve fitting process to the position and the amplitude of each of the peaks. The system may also determine a time-offset value for a peak based on its position in relation to a previous peak, and may transmit the energy values and corresponding times to generate time-coincident pairs for image reconstruction.

20 Claims, 11 Drawing Sheets

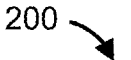
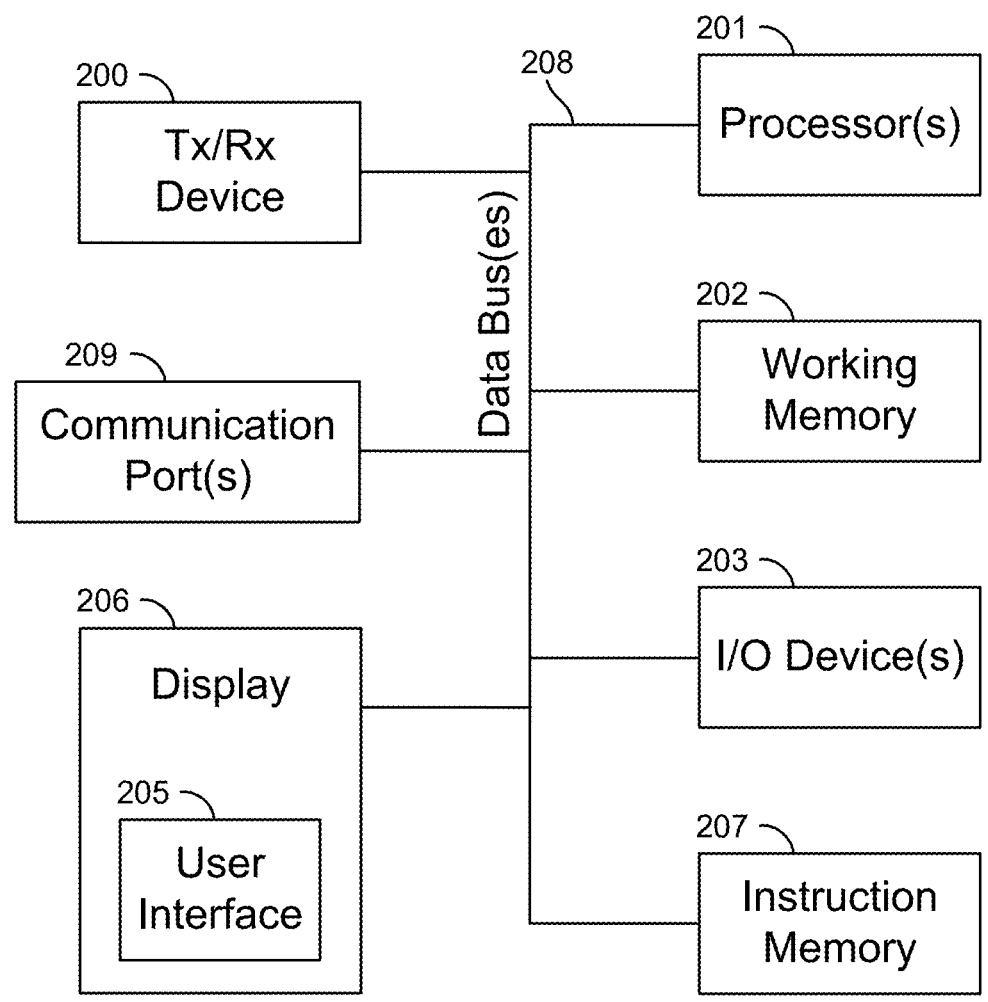
FIG. 2

400

START

RECEIVE A SIGNAL OF A DETECTED EVENT — 402

DETECT A POSITION AND AN AMPLITUDE OF AT LEAST TWO PEAKS OF THE SIGNAL — 404

BASED ON APPLYING A CURVE FITTING PROCESS TO THE POSITIONS AND AMPLITUDES, GENERATE FIRST PULSE DATA CHARACTERIZING A FIRST PULSE AND SECOND PULSE DATA CHARACTERIZING A SECOND PULSE — 406

TRANSMIT THE FIRST PULSE DATA AND THE SECOND PULSE DATA — 408

END

START

RECEIVE FIRST LOCATION VALUES AND FIRST POSITION VALUES OF AT LEAST TWO PEAKS OF AN ENERGY SIGNAL, SECOND LOCATION VALUES AND SECOND POSITION VALUES OF AT LEAST TWO PEAKS OF A FIRST LOCATION SIGNAL, AND THIRD LOCATION VALUES AND THIRD POSITION VALUES OF AT LEAST TWO PEAKS OF A SECOND LOCATION SIGNAL ⌐502

APPLY A CURVE FITTING PROCESS TO THE FIRST LOCATION VALUES AND FIRST POSITION VALUES AND, BASED ON THE APPLICATION OF THE CURVE FITTING PROCESS, GENERATE FIRST ENERGY PULSE DATA CHARACTERING A FIRST PULSE, AND SECOND ENERGY PULSE DATA CHARACTERIZING A SECOND PULSE ⌐504

APPLY THE CURVE FITTING PROCESS TO THE SECOND LOCATION VALUES AND SECOND POSITION VALUES AND, BASED ON THE APPLICATION OF THE CURVE FITTING PROCESS, GENERATE FIRST LOCATION FIRST PULSE DATA CHARACTERING A FIRST PULSE, AND FIRST LOCATION SECOND PULSE DATA CHARACTERIZING A SECOND PULSE ⌐506

APPLY THE CURVE FITTING PROCESS TO THE THIRD LOCATION VALUES AND THIRD POSITION VALUES AND, BASED ON THE APPLICATION OF THE CURVE FITTING PROCESS, GENERATE SECOND LOCATION FIRST PULSE DATA CHARACTERING A FIRST PULSE, AND SECOND LOCATION SECOND PULSE DATA CHARACTERIZING A SECOND PULSE ⌐508

DETERMINE A FIRST PULSE TIME OFFSET VALUE BASED ON THE FIRST POSITION VALUES, A SECOND PULSE TIME OFFSET VALUE BASED ON THE SECOND POSITION VALUES, AND A THIRD PULSE TIME OFFSET VALUE BASED ON THE THIRD POSITION VALUES ⌐510

TRANSMIT THE FIRST ENERGY PULSE DATA, THE SECOND ENERGY PULSE DATA, THE FIRST LOCATION FIRST PULSE DATA, THE SECOND LOCATION FIRST PULSE DATA, THE FIRST LOCATION SECOND PULSE DATA, THE SECOND LOCATION SECOND PULSE DATA, THE FIRST PULSE TIME OFFSET VALUE, THE SECOND PULSE TIME OFFSET VALUE, AND THE THIRD PULSE TIME OFFSET VALUE ⌐512

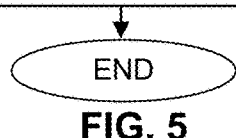

END

FIG. 5

METHODS AND APPARATUS FOR MEDICAL IMAGING EVENT DETECTION AND IMAGE RECONSTRUCTION

FIELD

Aspects of the present disclosure relate in general to medical diagnostic systems and, more particularly, to capturing and reconstructing images from nuclear imaging systems for diagnostic and reporting purposes.

BACKGROUND

Nuclear imaging systems can employ various technologies to capture images. For example, some nuclear imaging systems employ positron emission tomography (PET) to capture images. PET is a nuclear medicine imaging technique that produces tomographic images representing the distribution of positron emitting isotopes within a body. Some nuclear imaging systems combine images from PET and a co-modality, such as computed tomography (CT) or Magnetic Resonance Imaging (MRI). CT is an imaging technique that uses x-rays to produce anatomical images. Magnetic Resonance Imaging (MRI) is an imaging technique that uses magnetic fields and radio waves to generate anatomical and functional images, and may also be used as a co-modality. These nuclear imaging systems can combine images from PET and co-modality scanners during an image fusion process to produce images that show information from both the PET scan and the co-modality scan (e.g., PET/CT systems). Moreover, the nuclear imaging systems may generate an attenuation map that can be used to correct the PET measurement data during image reconstruction.

Typically, PET systems (e.g., time-of-flight (TOF) PET systems) include a scanner with detector elements that include crystals which can detect gamma rays during the scanning process. The detector elements include crystals that detect the gamma rays. The systems can generate measurement data characterizing an image based on these detections. Sometimes, however, these systems ignore or miss detection events when, for instance, multiple detection events occur near each other in time. As a result, the generated measurement data may suffer in accuracy, as well as any medical image reconstructed based on the measurement data. As such, there are opportunities to address these and other deficiencies in nuclear imaging systems.

SUMMARY

Systems and methods for detecting multiple events during nuclear imaging scans, and for reconstructing medical images based on the detected events, are disclosed.

In some embodiments, a computer-implemented method includes receiving at least one signal characterizing a detection event. The method also includes applying a peak detection process to the at least one signal and, based on the application of the peak detection process, detecting a position of each of at least two peaks of the at least one signal. Further, the method includes determining an amplitude of each of the at least two peaks of the at least one signal. The method also includes applying a curve fitting process to the position and the amplitude of each of the at least two peaks and, based on the application of the curve fitting process, determining an energy value for each of the at least two peaks. The method further includes transmitting the energy value for each of the at least two peaks.

In some embodiments, a non-transitory computer readable medium stores instructions that, when executed by at least one processor, cause the at least one processor to perform operations including receiving at least one signal characterizing a detection event. The operations also include applying a peak detection process to the at least one signal and, based on the application of the peak detection process, detecting a position of each of at least two peaks of the at least one signal. Further, the operations include determining an amplitude of each of the at least two peaks of the at least one signal. The operations also include applying a curve fitting process to the position and the amplitude of each of the at least two peaks and, based on the application of the curve fitting process, determining an energy value for each of the at least two peaks. The operations further include transmitting the energy value for each of the at least two peaks In some embodiments, a system includes a memory device storing instructions, a transceiver, and at least one processor communicatively coupled the transceiver and the memory device. The at least one processor is configured to execute the instructions to receive, via the transceiver, at least one signal characterizing a detection event. The at least one processor is also configured to execute the instructions to apply a peak detection process to the at least one signal and, based on the application of the peak detection process, detect a position of each of at least two peaks of the at least one signal. Further, the at least one processor is configured to execute the instructions to determine an amplitude of each of the at least two peaks of the at least one signal. The at least one processor is also configured to execute the instructions to apply a curve fitting process to the position and the amplitude of each of the at least two peaks and, based on the application of the curve fitting process, determine an energy value for each of the at least two peaks. The at least one processor is further configured to execute the instructions to transmit, via the transceiver, the energy value for each of the at least two peaks.

BRIEF DESCRIPTION OF THE DRAWINGS

The following will be apparent from elements of the figures, which are provided for illustrative purposes and are not necessarily drawn to scale.

FIG. 2 illustrates a block diagram of an example computing device that can perform one or more of the functions described herein, in accordance with some embodiments.

FIG. 5 is a flowchart of an example method to generate data characterizing energy and location values for multiple pulses, in accordance with some embodiments.

DETAILED DESCRIPTION

Figure 1A:
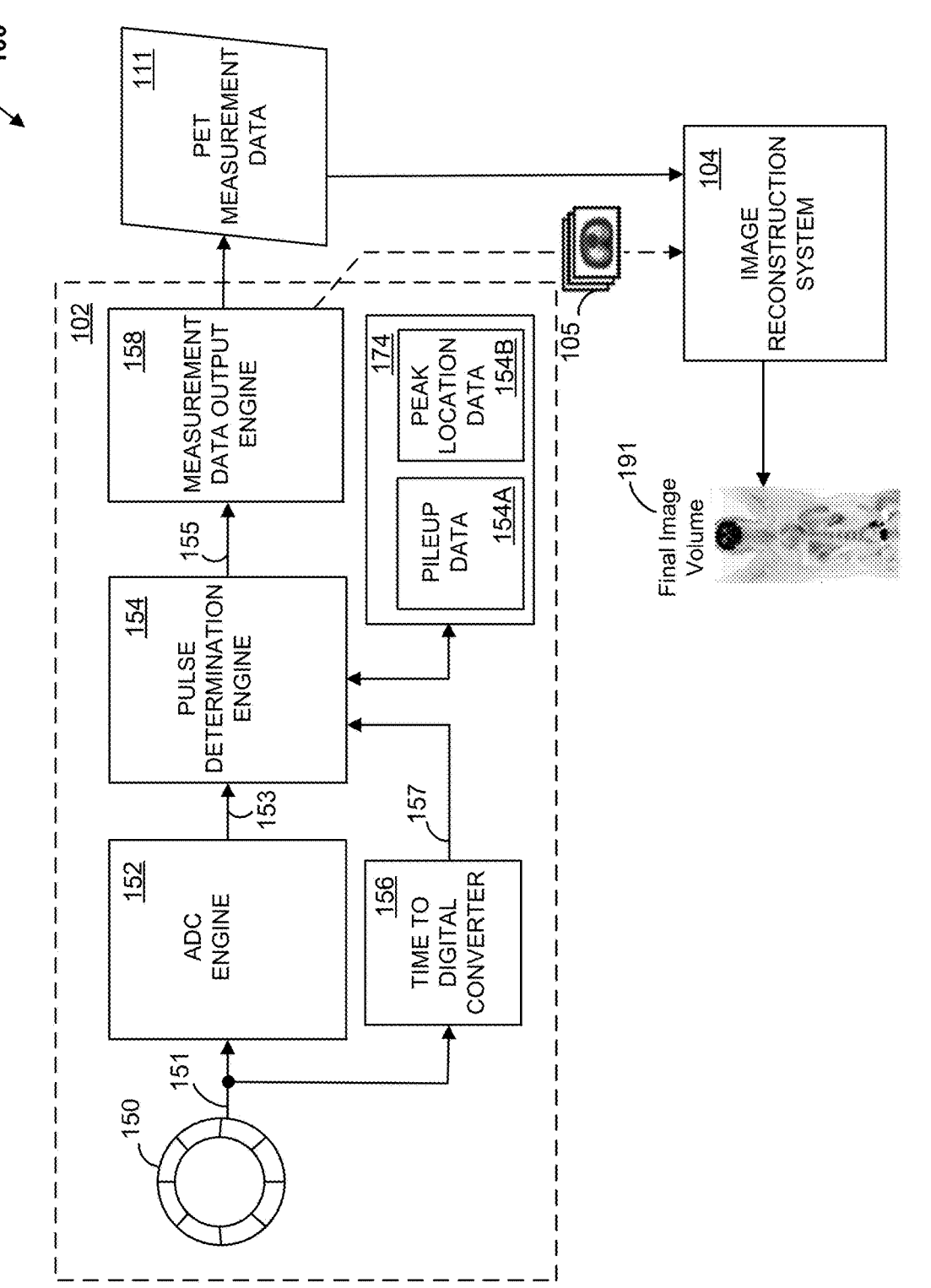
FIGS. 1A, 1B, and 1C illustrate a nuclear imaging system, in accordance with some embodiments.

This description of the exemplary embodiments is intended to be read in connection with the accompanying drawings, which are to be considered part of the entire written description. Independent of the grammatical term usage, individuals with male, female, or other gender identities are included within the term.

The exemplary embodiments are described with respect to the claimed systems as well as with respect to the claimed methods. Furthermore, the exemplary embodiments are described with respect to methods and systems for image reconstruction, as well as with respect to methods and systems for training functions used for image reconstruction. Features, advantages, or alternative embodiments herein can be assigned to the other claimed objects and vice versa. For example, claims for the providing systems can be improved with features described or claimed in the context of the methods, and vice versa. In addition, the functional features of described or claimed methods are embodied by objective units of a providing system. Similarly, claims for methods and systems for training image reconstruction functions can be improved with features described or claimed in context of the methods and systems for image reconstruction, and vice versa.

Various embodiments of the present disclosure can employ machine learning methods or processes to provide clinical information from nuclear imaging systems. For example, the embodiments can employ machine learning methods or processes to reconstruct images based on captured measurement data, and provide the reconstructed images for clinical diagnosis. In some embodiments, machine learning methods or processes are trained, to improve the reconstruction of images.

Positron emission tomography (PET) imaging systems can include a scanner with various detection elements. Each detection element may house crystals that detect emitted gamma rays from a scanned subject. When a crystal detects an event, one or more signals may be generated. For example, the system may generate a first signal characterizing an energy associated with the detected event. The system may additionally generate a second signal characterizing a first dimension location of the detection (e.g., X-axis location of the detecting crystal), and a third signal characterizing a second dimension location of the detection (e.g., a Y-axis location of the detecting crystal).

Each of any of these signals (e.g., first signal, second signal, and third signal) may characterize a pulse, where the height of the signal at any given point in time indicates an associated energy value, such as a kilo-electron volt (KeV) value. The energy of a radiation pulse can be measured by the area under the pulse of a particular event. As activity increases in the field-of-view of a systems' scanner, the probability of more than one pulse being generated simultaneously or nearly simultaneously increases. For instance, the scanner may detect a second pulse during a first pulse's duration, or while the scanner is processing the first pulse (e.g., within the pulse processing time of the scanner). Such a situation is referred to as "pileup." Conventional systems may attempt to detect such circumstances and, if detected, discard the detected event (e.g., do not process the detected event, as if it never happened). The conventional systems may discard such events to prevent introducing errors in energy and detector position (e.g., crystal position) estimates, or because of a lack of timing information associated with such an event. However, discarding such information reduces a system's sensitivity and, as a result, the accuracy of energy and position estimates.

The embodiments described herein employ pileup recovery processes that detect pileup events, decouple multiple pulses from the pileup events, and generate energy, position, and time (e.g., timestamp) estimates for each of the multiple pulses. For example, a single pulse shape can be described mathematically defined by a function. Function 1, below, illustrates a function Y(t) that characterizes a pulse.

$$Y(t) = Ks * \exp\big((-1 * (t - Ki)/tf)\big)/\big(1 + \exp(-1 * (t - Ki)/tr)\big) \quad (1)$$

Figure 6A:
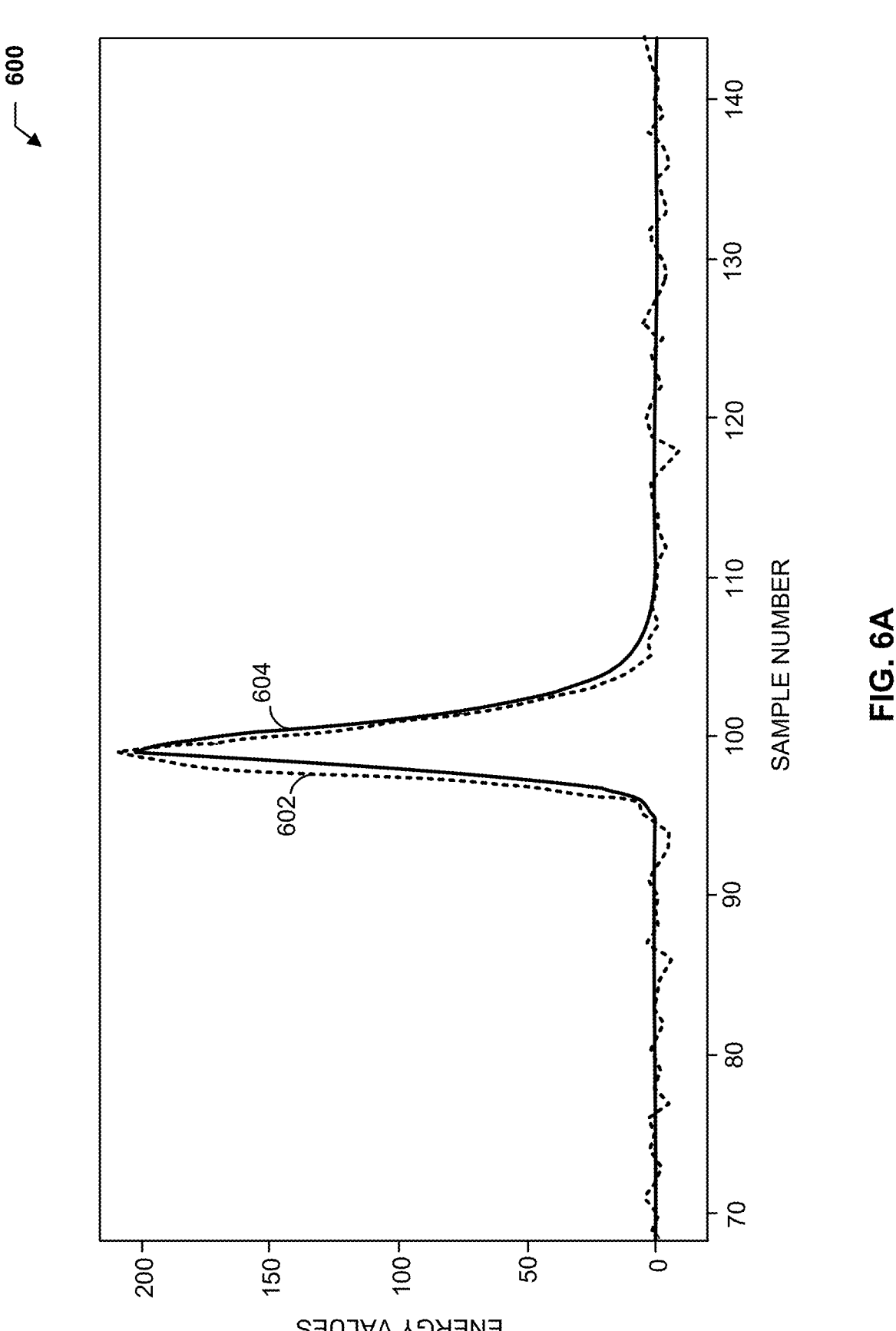
FIGS. 6A and 6B illustrate exemplary real and analytical pulses, in accordance with some embodiments.
Figure 6B:
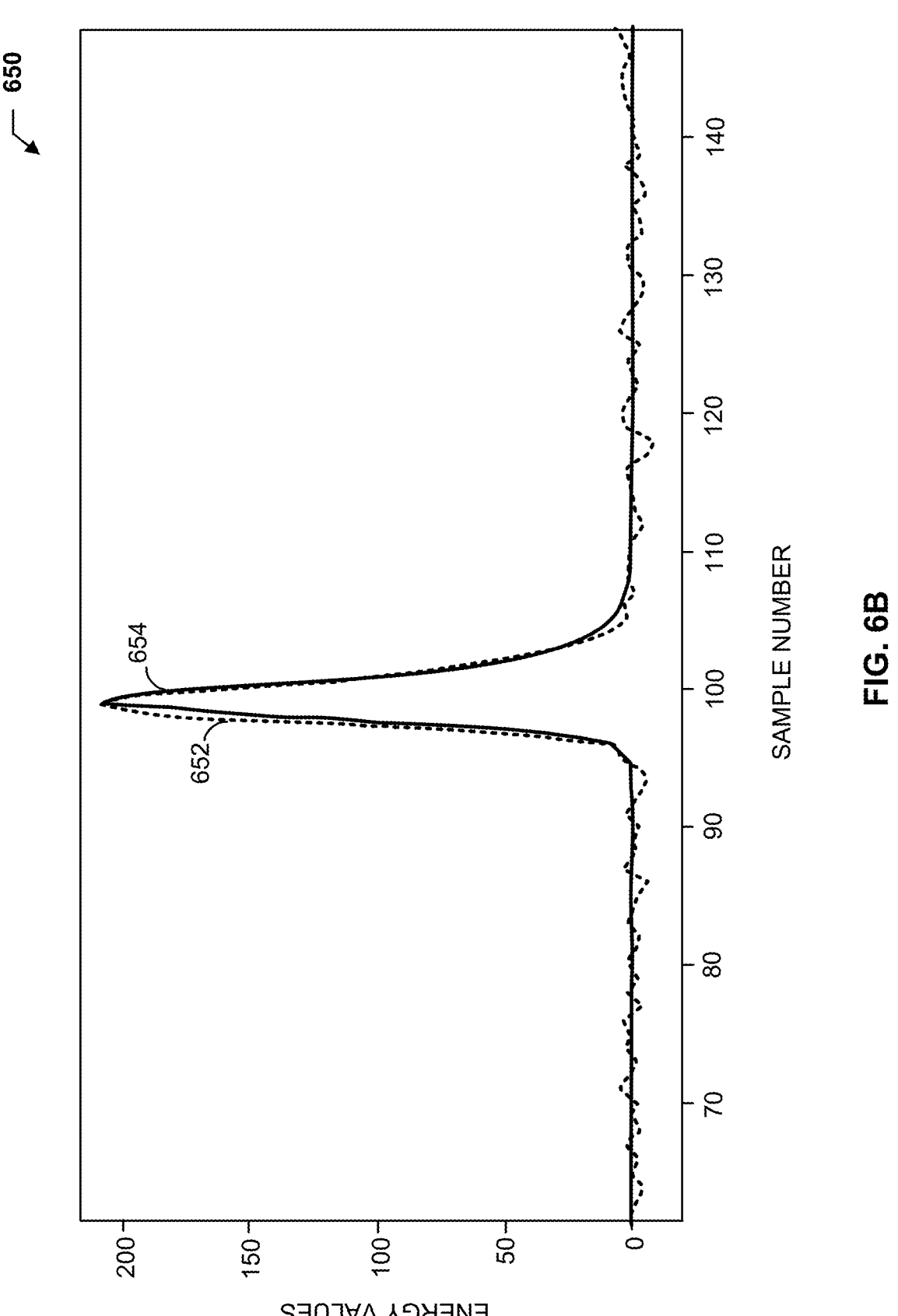

Here, the variable t represents time, the variable Ks is a global scale factor, the variable Ki is a time-offset term, the variable tf is a decay time constant for the pulse, and the variable tr is a rise time constant for the pulse. FIG. 6A, for example, illustrates a chart 600 that identifies sample numbers (e.g., analog-to-digital converter (ADC) sample numbers) along the X-axis and energy values (e.g., ADC sampled values) along the Y-axis. The chart 600 includes a captured pulse 602 illustrated in dashed lines overlaid with an analytical pulse 604 illustrated in a solid line. The analytical pulse 604 was computed using function 1 above with corresponding values for Ks, Ki, tf, and tr. Similarly, FIG. 6B illustrates a chart 650 with a captured pulse 652 illustrated in dashed lines overlaid with an analytical pulse 654 illustrated in a solid line. The analytical pulse 654 was also computed using function 1 above with the same values for Ks, Ki, tf, and tr. As indicated by each of these figures, the analytical pulses 604, 654, closely match the captured pulses 602, 652, respectively.

Figure 7A:
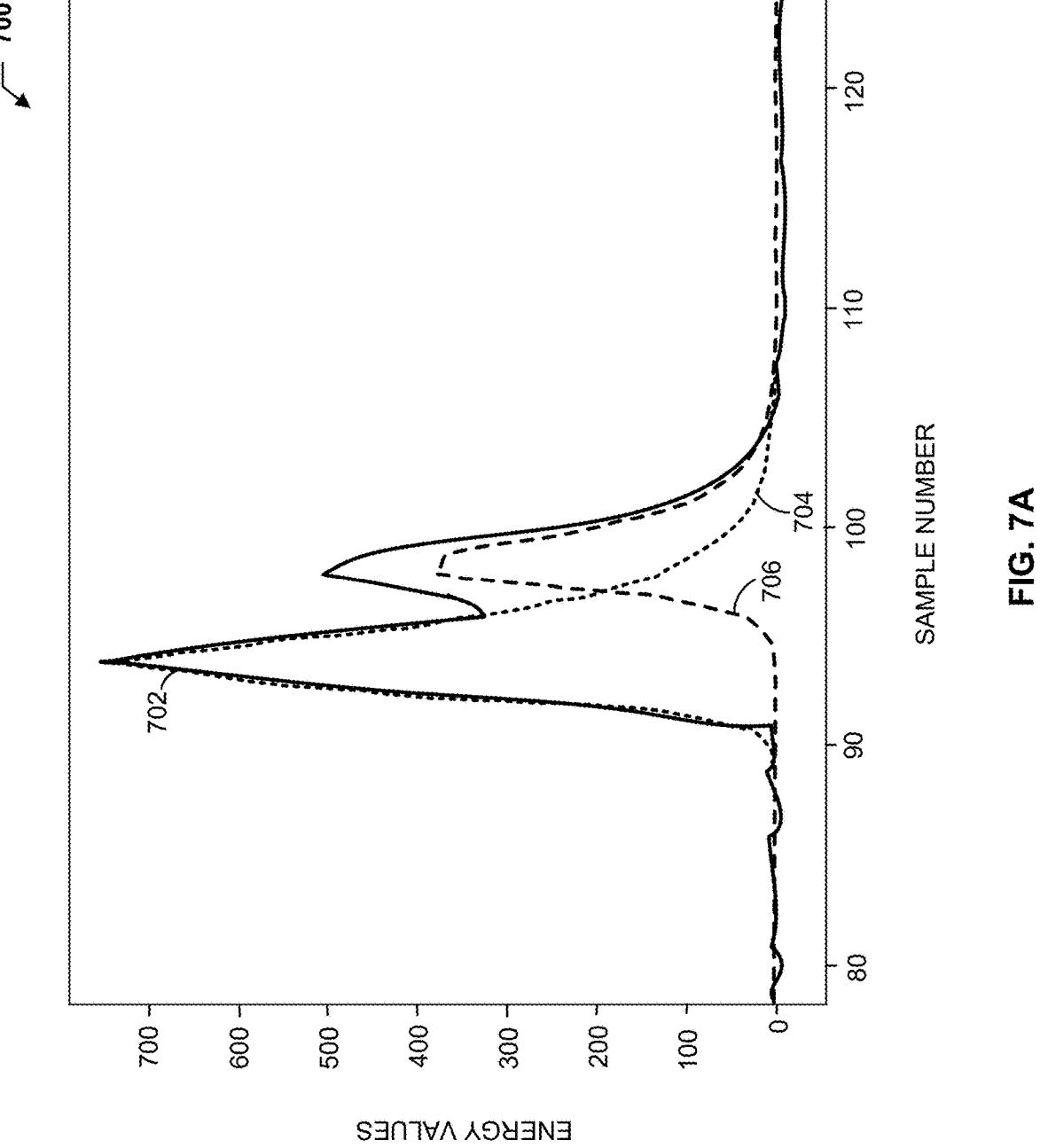
FIGS. 7A and 7B illustrate two pulses fitted to a pileup pulse, in accordance with some embodiments.

Further, FIG. 7A illustrates a chart 700 that also identifies sample numbers along the X-axis and energy values (e.g., ADC sampled values) along the Y-axis. The chart 700 shows a pileup signal 702 as a solid line, which is a signal that may be received when two events are detected simultaneously or nearly simultaneously. For instance, the pileup signal 702 may result when one event is detected while the scanner is still processing a signal from a previously detected event (e.g., before the first signal has completely decayed). Function 2, below, characterizes a pileup signal, such as pileup signal 702, as the sum of two or more individual pulses, where each individual pulse is characterized by Function 1.

$$P(t) = Y0(t) + Y1(t) + \ldots + Yn(t) \quad (2)$$

Figure 7B:
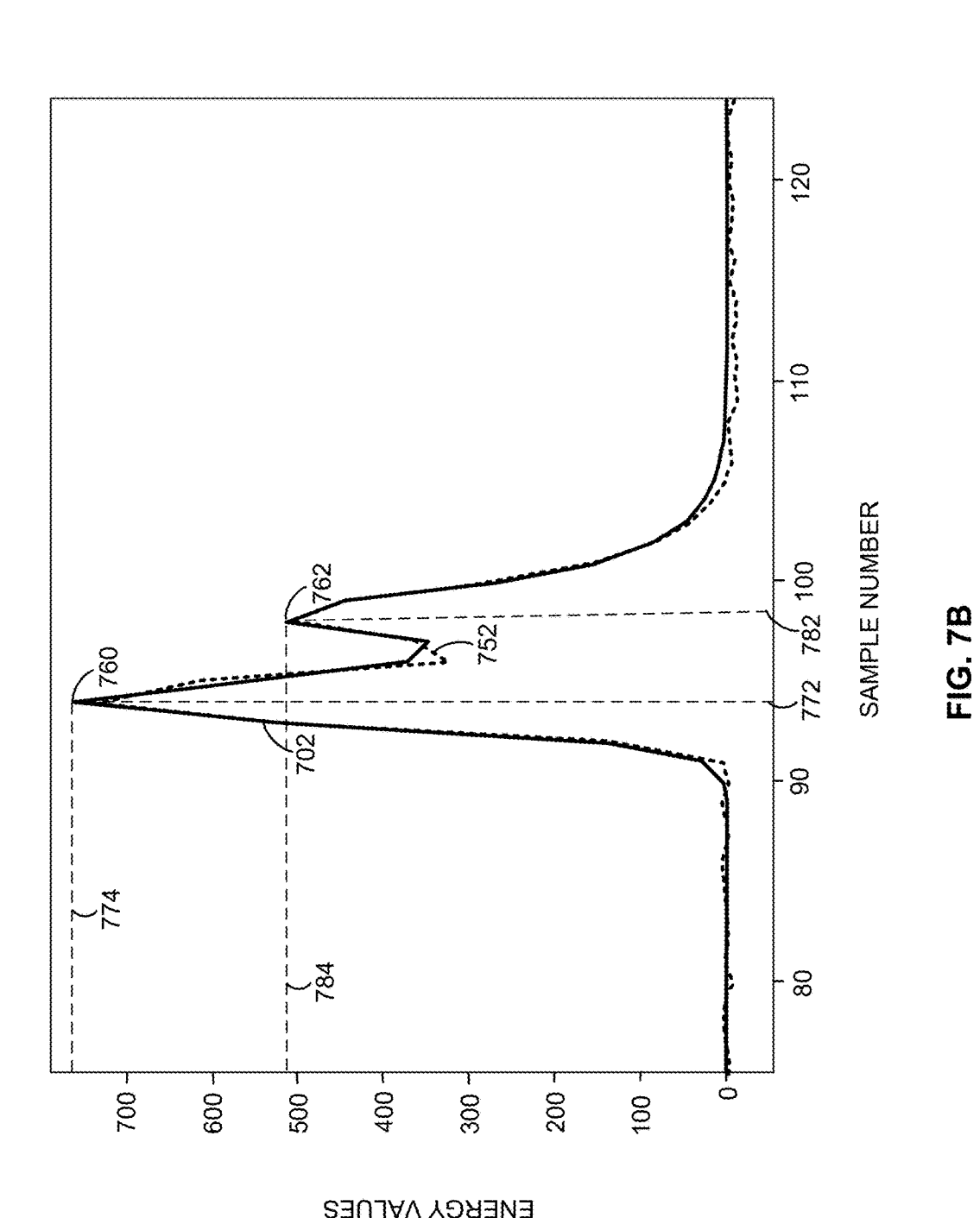

To decouple two or more pulses from a pileup signal, such as pileup signal 702, the embodiments described herein may apply a curve fitting process (e.g., execution of a curve fitting algorithm) to the pileup signal to generate data characterizing two or more individual pulses. For example, the embodiments may fit $\Sigma nP(t)$ to the pileup signal to decouple the individual pulses. In some examples, the embodiments may fit $\Sigma nP(t)$ to the pileup signal based on a least squares means, Levenberg-Marquardt, or any other suitable algorithm to decouple the individual pulses. For instance, and based on a curve fitting process applied to the pileup signal 702, a first decoupled pulse 704 and a second decoupled pulse 706 may be determined. FIG. 7B illustrates a chart 750 showing the pileup signal 702, as well as summation pulse 752, which is the summation of the first decoupled pulse 704 and the second decoupled pulse 706. FIG. 7B illustrates that the first decoupled pulse 704 and the second decoupled pulse 706, when added to each other (e.g., according to Function 2), closely match the original pileup signal 702.

To execute the curve fitting process, in some examples, a peak detection process is applied to the pileup signal 702 to determine (e.g., approximate) a location of each of multiple (e.g., two) peaks. For instance, and with reference to FIG. 7B, peak detection process may include detecting first peak 760 and second peak 762 of the pileup signal 702. For instance, the peak detection process may include detecting that the pileup signal's 702 amplitude decreases (e.g., the signal has a negative slope) over a minimum amount of time after having increased (e.g., the signal has a positive slope) for a same, or different, minimum amount of time. In some examples, the peak detection process also includes determining that the pileup signal's 702 amplitude does not drop below a minimum signal amplitude between peaks.

The peak detection process may also include determining a corresponding sample number 772, 782 (ADC sample numbers) for each of the first peak 760 and the second peak 762. The sample numbers 772, 782 provide a location of each of the first peak 760 and the second peak 762. The peak detection process may also detect a height 774, 784 (e.g., amplitude) of each of the first peak 760 and the second peak 762. Once the peak locations and heights are determined, the curve fitting process may include inputting the peak locations and the peak heights to an executed curve fitting model, such as one based on least square means. Based on the inputted peak locations and peak heights, the curve fitting process may include generating, by the executed curve fitting model, output data characterizing individual pulse parameters, such as values for Ks, Ki, tf, and tr for function 1 for each of the individual pulses. In some examples, the embodiments may assign constant values to one or more of tf and tr. As such, the curve fitting model would only return Ks and Ki for function 1.

Further, and based on the individual pulse parameters for each pulse, the embodiments may determine an energy value for each pulse. For instance, the embodiments may determine an area under each detected peak, or may apply any suitable peak detection process to detect a peak value of the pulse, among other examples. In some examples, the embodiments may execute Function 1 using each of the individual pulse parameters to determine an energy value, e.g., Y(t), for each corresponding pulse. The embodiments may perform these processes for any signals received from a scanner, such as the first signal characterizing energy, and the second signal and third signal characterizing crystal locations, as described herein.

Further, the embodiments may determine a time (e.g., timestamp) associated with each pulse (e.g., each pulse generated for each of the various signals received from a scanner, such as the first signal characterizing energy, and the second signal and third signal characterizing crystal locations). For example, the embodiments may determine a location offset (e.g., sample number difference) between the peaks (e.g., between first peak 760 and second peak 762), and may determine the time associated with each pulse based on the location offset. As an example, assume the sample number 782 of the second peak 762 is 98 and the sample number 772 of the first peak 760 is 93. The offset between the first peak 760 and the second peak 762 may be 5 (98–93), where 5 indicates time in terms of the ADC sampling rate. A first time may be assigned to the first decoupled pulse 704 upon pulse detection (e.g., when the signal amplitude reaches a threshold amplitude level), and a second time may be assigned to the second decoupled pulse 706 based on the first time and the offset. For instance, the second time may be the offset added to the first time. The energy values and corresponding times may then be employed to reconstruct an image.

Referring now to FIG. 1A, a nuclear imaging system 100 includes an image scanning system 102 and an image reconstruction system 104. Image scanning system 102 may be a PET scanner that can capture PET images, a PET/MR scanner that can capture PET and MR images, a PET/CT scanner that can capture PET and CT images, or any other suitable image scanner. For example, image scanning system 102 can capture PET images (e.g., of a person), and can generate PET measurement data 111 based on the captured PET images. The PET measurement data 111 (e.g., sinogram data, list-mode data) can represent anything imaged in the scanner's field-of-view (FOV) containing positron emitting isotopes. Moreover, the PET measurement data 111 may identify detection events (e.g., time-coincident pair data) and related timing information. The image scanning system 102 can transmit the PET measurement data 111 to the image reconstruction system 104 for image reconstruction. For example, the image reconstruction system 104 may apply machine learning processes to the PET measurement data to generate a final image volume 191 characterizing a reconstructed image.

In some examples, image scanning system 102 may additionally generate attenuation maps 105 (e.g., μ-maps). For instance, the image scanning system 102 may be a PET/CT scanner that, in addition to PET images, can capture CT scans of the patient. The image scanning system 102 may generate the attenuation maps 105 based on the captured CT images, and may transmit the attenuation maps 105 to the image reconstruction system 104. As another example, the image scanning system 102 may be a PET/MR scanner that, in addition to PET images, can capture MR scans of the patient. The image scanning system 102 may generate the attenuation maps 105 based on the captured MR images, and may transmit the attenuation maps 105 to the image reconstruction system 104.

In this example, image scanning system 102 includes a scanner 150, an analog-to-digital-converter (ADC) engine 152, a pulse determination engine 154, a time to digital converter (TDC) 156, and a measurement data output engine 158. In some examples, all or parts of image scanning system 102 are implemented in hardware, such as in one or more field-programmable gate arrays (FPGAs), one or more application-specific integrated circuits (ASICs), one or more state machines, one or more computing devices, digital circuitry, or any other suitable circuitry. For example, all or parts of ADC engine 152, pulse determination engine 154, TDC 156, and measurement data output engine 158 may be implemented within one or more FPGAs. In some examples, parts or all of image scanning system 102 can be implemented in software as executable instructions such that, when executed by one or more processors, cause the one or more processors to perform respective functions as described herein. The instructions can be stored in a non-transitory, computer-readable storage medium, and can be read and executed by the one or more processors.

The scanner 150 may include detector elements that include crystals which can detect gamma rays during the scanning (e.g., imaging) process. Specifically, for each detection event, scanner 150 may generate detection data 151 that includes one or more signals (e.g., for one or more detection channels). For example, detection data 151 may include a first signal characterizing detected energy levels (e.g., energy depositions), a second signal characterizing a first dimension position of the detecting crystal, and/or a third signal characterizing a second dimension position of the detecting crystal. The scanner 150 may provide the detection data 151 characterizing detected events to ADC engine 152.

ADC engine 152 may include an analog-to-digital converter (ADC) that samples each signal characterized by the detection data 151 at a sample rate to generate ADC data 153 characterizing the sampled signal. For example, ADC engine 152 may sample each signal at a corresponding Nyquist rate, such as every 20 nano-seconds, and, based on the sampling, may generate ADC data 153 characterizing corresponding voltage levels for the signal. ADC engine 152 may transmit the ADC data 153 for each signal characterized by the detection data 151 to pulse determination engine 154.

Pulse determination engine 154 may receive the ADC data 153, and may determine that a corresponding signal includes a signal pileup when the ADC data 153 includes sampled values that are above a predetermined threshold voltage level for at least a predetermined amount of time (e.g., 20 ADC samples). In some examples, pulse determination engine 154 may detect peaks based on the ADC data 153, and may further determine the corresponding signal includes a signal pileup when two or more peaks are detected. For example, pulse determination engine 154 may detect peaks based on a highest ADV data 153 value. As another example, to detect peaks, pulse determination engine 154 may detect decreasing ADC data 153 values (e.g., a portion of the ADC data 153 has a negative slope) over a minimum number of samples (e.g., amount of time) after detecting ADC data 153 values that increased (e.g., a previous portion of ADC data 153 has a positive slope) for a same, or different, number of samples. In some examples, to detect a signal pileup, pulse determination engine 154, additionally or alternatively, determines that the ADC data 153 values do not drop below a minimum amplitude between detected peaks. Other methods of detecting peaks are also contemplated herein.

Pulse determination engine 154 may generate pileup data 154A indicating whether or not a pileup was detected for each signal characterized by the detection data 151. For instance, pileup data 154A may include a bit for each signal, where each bit identifies whether a pileup was detected for the corresponding signal. As an example, a value of 0x0 may indicate no pileup, a value of 0x1 may indicate a pileup of the first signal, a value of 0x2 may indicate a pileup of the second signal, and a value of 0x3 may indicate a pileup of the first and second signals. Similarly, a value of 0x4 may indicate a pileup of the third signal, a value of 0x5 may indicate a pileup of the first and third signals, a value of 0x6 may indicate a pileup of the second and third signals, and a value of 0x7 may indicate a pileup of the first, second, and third signals.

Pulse determination engine 154 may also generate peak location data 154B identifying a location of each detected peak for each of the signals. For example, the peak location data 154B may identify an ADC sample number, or a range of ADC sample numbers, of the ADC data 153 corresponding to each detected peak. Pulse determination engine 154 may store the pileup data 154A and peak location data 154B within a memory device 174, for example.

Further, pulse determination engine 154 may perform processes to decouple two or more pulses from the ADC data 153. For example, when a pileup event is detected, pulse determination engine 154 may apply a curve fitting process to the ADC data 153 for each detected peak identified by the peak location data 154B and, based on the application of the curve fitting process, pulse determination engine 154 may determine a pulse (e.g., signal) for each detected peak. For instance, pulse determination engine 154 may determine an amplitude for each detected peak based on corresponding ADC data 153. Further, pulse determination engine 154 may apply a curve fitting process to the position and amplitude of each of at least two detected peaks and, based on the application of the curve fitting process, determine a pulse (e.g., signal) for each of the at least two peaks. For instance, pulse determination engine 154 may input the peak locations and the peak amplitudes to an executed curve fitting model. Based on the inputted peak locations and peak amplitudes, the executed curve fitting model may generate output data characterizing individual pulse parameters for corresponding pulses, such as values for Ks, Ki, and, optionally, tf, and tr, for function 1 for each of the at least two detected peaks. In some examples, pulse determination engine 154 may include a lookup table (e.g., stored in memory) that maps ranges of peak locations and ranges of peak amplitudes to pulse parameters. Pulse determination engine 154 may obtain the pulse parameters from the lookup table based on the peak locations and peak amplitudes.

Further, and based on the pulse parameters, the pulse determination engine 154 may generate energy values characterizing each of the at least two pulses. For instance, for each pulse characterized by ADC data 153 for which a pileup has been detected, pulse determination engine 154 may determine an energy value. The energy value may be determined based on an area under a curve of each peak. As an example, pulse determination engine 154 may execute function 1 based on the corresponding pulse parameters to determine an energy value Y(t) at each peak location. In some examples, pulse determination engine 154 determines an event occurred when the energy value is within a range, such as above a lower discriminator and below an upper discriminator. If the energy value is not within the range, pulse determination engine 154 may discard (e.g., ignore) the event.

As an example, pileup data 154A may indicate that a pileup has been detected for each of an energy signal, first dimension location signal, and second dimension location signal of the detection data 151. Pulse determination engine 154 may perform the processes described above for each of the three signals to detect two pulses on each of the three signals, and may further determine energy values at the locations of the peaks of each of the two pulses on each of the three signals. Pulse determination engine 154 may generate pulse data 155 characterizing the energy values for each of the two pulses on each of the three signals.

As illustrated, pulse determination engine 154 may also receive time data 157 from TDC 156. The time data 157 may characterize a time associated with each detection event received for the one or more signals of the detection data 151. For instance, TDC 156 may receive the detection data 151 and generate, for each detection event of each signal of the detection data 151, time data 157 characterizing a digital time. For example, in response to receiving a detection event on a signal of detection data 151, TDC 156 may sample a system time and, based on the sampled system time, generate time data 157 for the signal. As described herein, detection data 151 may characterize events detected for one or more signals (e.g., one or more detection channels). As such, TDC 156 may generate time data 157 for each of the one or more signals when an event is received. For instance, in response to each received event, TDC 156 may generate time data 157 for that event. TDC 156 may transmit the time data 157 to pulse determination engine 154.

Pulse determination engine 154 may receive the time data 157 and, based on the time data 157, determine a time for each pulse detected on the corresponding signal of the detection data 151. For instance, pulse determination engine 154 may determine a first time for a first pulse (earlier pulse) based on the time data 157, and may generate a second time for a second pulse (later, generated pulse) based on the first time and a corresponding offset value, where the offset value is determined from peak location data 154B. For example, pulse determination engine 154 may determine an offset value between two pulses based on the peak locations of the pulses identified by the peak location data 154B. For instance, each offset value may be based on a difference (e.g., sample number difference) between the peak locations of the two pulses. In the example where the offset value represents a difference in sample numbers, pulse determination engine 154 may scale the offset value to the system time (e.g., to same units as the system time), and add the scaled offset value to the first time to generate the second time.

In addition to characterizing energy values for one or more detected pulses, pulse determination engine 154 may generate the pulse data 155 to characterize corresponding times (e.g., timestamps) for each pulse on each signal. For instance, pulse data 155 may include pulse-time pairs, where each pulse-time pair characterizes a detected pulse and a corresponding time associated with the detected pulse. Pulse determination engine 154 may transmit the pulse data 155 to measurement data output engine 158.

Measurement data output engine 158 may receive the pulse data 155 from the pulse determination engine 154. Based on the pulse data 155, measurement data output engine 158 may generate PET measurement data 111. The PET measurement data 111 identifies detected crystal pulses (e.g., time-coincident data pairs) as well as corresponding times (e.g., time offsets between detection events). For example, the measurement data output engine 158 may perform processes to generate time-coincident pairs based on the times and pulses identified by the pulse data 155, and may generate the PET measurement data 111 to include the determined time-coincident pairs.

Further, and as illustrated, image reconstruction system 104 may receive the PET measurement data 111 form the image scanning system 102. Image reconstruction system 104 may perform operations to reconstruct an image based on the PET measurement data 111, and may generate final image volume 191 characterizing the reconstructed image. For example, image reconstruction system 104 may apply one or more trained machine learning processes to the PET measurement data 111 and, based on applying the one or more trained machine learning processes, may generate the final image volume 191. In some instances, image reconstruction system 104 receives an attenuation map 105 from the image scanning system 102. The image reconstruction system 104 may perform operations to correct the PET measurement data 111, for example for attenuation, based on the attenuation map 105. For instance, the image reconstruction system 104 may apply one or more attenuation correction processes to the output of the trained machine learning process and the attenuation map 105 and, based on applying the one or more attenuation correction processes, may generate the final image volume 191.

Image reconstruction system 104 may transmit the final image volume 191 characterizing the reconstructed image. For instance, image reconstruction system 104 and may transmit the final image volume 191 for display, and/or may store the final image volume within a data repository.

Figure 1B:
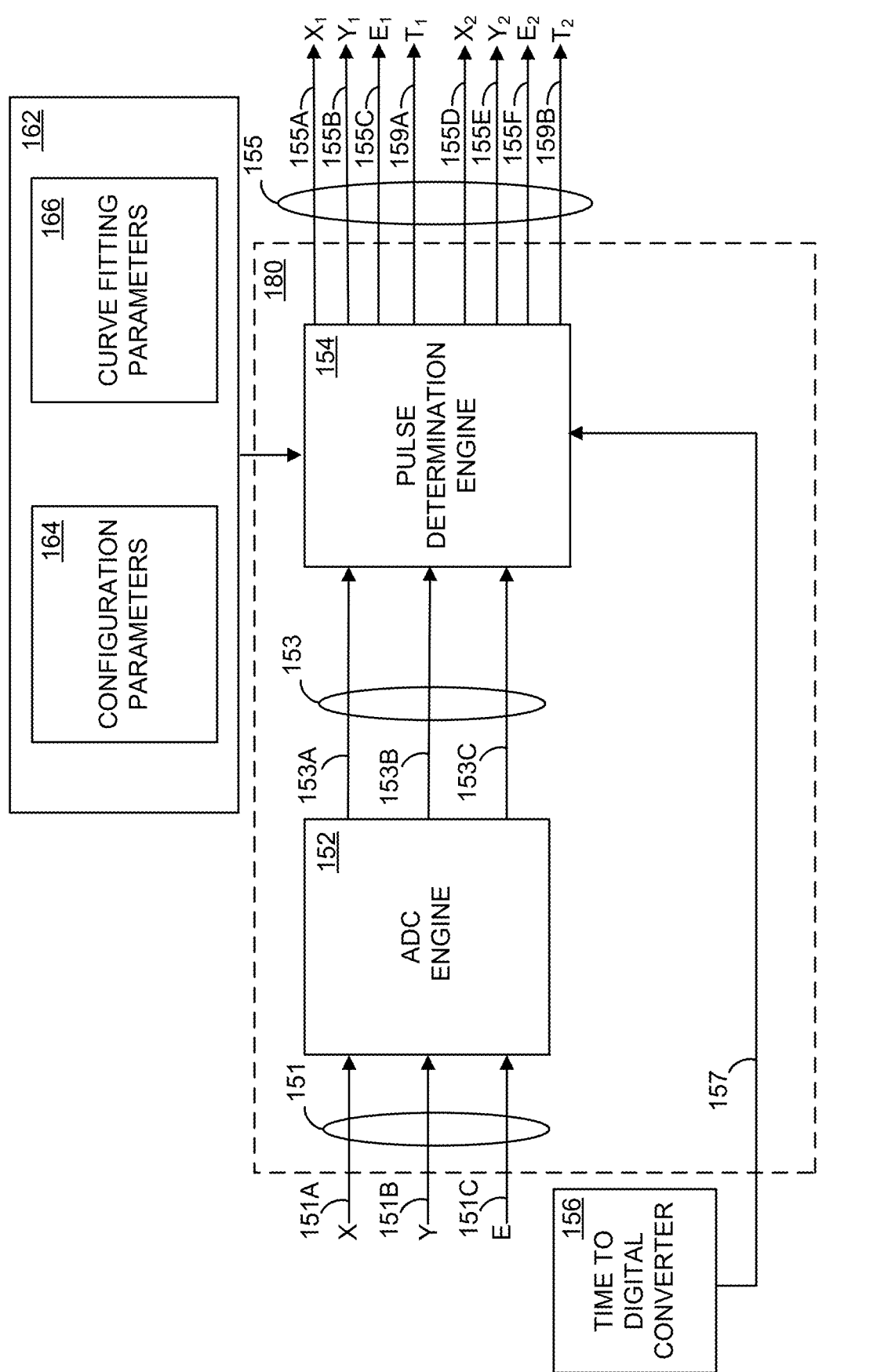

FIG. 1B illustrates exemplary portions of image scanning system 102 including an example of ADC engine 152 and pulse determination engine 154 communicatively coupled to a memory 162. Memory 162 may store configuration parameters 164 and curve fitting parameters 166. Configuration parameters 164 may include values to configure one or more of the ADC engine 152 and pulse determination engine 154, while curve fitting parameters 166 may include parameters that characterize a curve fitting model.

As described herein, ADC engine 152 may receive detection data 151 characterizing events detected by scanner 150. For example, detection data 151 may include a first dimension location signal 151A, a second dimension location signal 151B, and an energy signal 151C. The first dimension location signal 151A may characterize a first dimension of a location of a crystal detecting an event (e.g., an X axis location), while the second dimension location signal 151B may characterize a second dimension of the location of the crystal detecting the event (e.g., a Y axis location). Further, the energy signal 151C may characterize an energy (e.g., energy levels) of the detected event. ADC engine 152 may sample each of the first dimension location signal 151A, second dimension location signal 151B, and energy signal 151C and, based on the sampling, generate ADC data 153 including first dimension ADC data 153A, second dimension ADC data 153B, and energy ADC data 153C, respectively. ADC engine 152 may transmit each of the first dimension ADC data 153A, second dimension ADC data 153B, and energy ADC data 153C to pulse determination engine 154.

As described herein, pulse determination engine 154 may perform operations to detect one or more pulses based on each of first dimension ADC data 153A, second dimension ADC data 153B, and energy ADC data 153C. In some examples, pulse determination engine 154 determines the number of peaks to detect based on configuration parameters 164. For example, configuration parameters 164 may include a "number of peaks" value identifying the number of peaks to detect for a pileup event. In some instances, the number of peaks value is two. In other instances, the number of peaks value is greater than two (e.g., 3, 4, etc.) pulse determination engine 154 may read the number of peaks value from the configuration parameters 164 stored in the memory, and may determine a pileup event when a number of peaks equal to or greater than the number of peaks value are detected on a signal.

Pulse determination engine 154 may determine, based on pileup data 154A, whether each of these signals (i.e., first dimension location signal 151A, second dimension location signal 151B, energy signal 151C) includes a pileup event, as described herein. If pulse determination engine 154 does not detect a pileup event for a signal, pulse determination engine 154 may output a location of the single event of the signal as a portion of pulse data 155. For example, if pulse determination engine 154 does not detect a pileup event for any of first dimension ADC data 153A, second dimension ADC data 153B, and energy ADC data 153C, pulse determination engine 154 may provide the first dimension ADC data 153A, second dimension ADC data 153B, and energy ADC data 153C as first pulse first dimension location 155A, first pulse second dimension location 155B, and first pulse energy value 155C, respectively. Pulse determination engine 154 may also generate first time data 159A based on corresponding time data 157 received from TDC 156. As described herein, the time data 157 generated by TDC 156 indicates a time when one or more of the first dimension location signal 151A, second dimension location signal 151B, energy signal 151C were detected by ADC 152. As such, the first time data 159A generated by pulse determination engine 154 characterizes a corresponding time (e.g., timestamp) associated with each of the first pulse first dimension location 155A, first pulse second dimension location 155B, and first pulse energy value 155C.

If, however, pulse determination engine 154 detects that a signal includes a pileup event, e.g., that the signal includes at least two peaks, pulse determination engine 154 may determine a location of each detected peak based on peak location data 154B. Pulse determination engine 154 may also detect an amplitude of the corresponding signal at each peak location. For example, and using energy signal 151C as an example, pulse determination engine 154 may determine an amplitude of the energy signal 151C at each peak location identified by peak location data 154B. Pulse determination engine 154 may then apply a curve fitting process to the position and the amplitude of each of the at least two peaks and, based on the application of the curve fitting process, determine an energy value for each of the at least two peaks. For example, curve fitting parameters 166 may characterize a curve fitting model, such as one based on least square means. Pulse determination engine 154 may read the curve fitting parameters 166 from the memory 162, and execute the curve fitting model based on the read curve fitting parameters 166. As described herein, the curve fitting process may include inputting the peak locations and the peak amplitudes to the executed curve fitting model. Based on the inputted peak locations and peak heights, the curve fitting process may include generating, by the executed curve fitting model, output data characterizing individual pulse parameters, such as values for Ks, Ki, tf, and tr for function 1 for each of one or more individual pulses. In some examples, pulse determinator 172 assigns constant values to one or more of tf and tr. For example, the constant values for each of tf and tr may be stored as curve fitting parameters 166 in memory 162. As such, the curve fitting model would only return Ks and Ki for function 1.

Further, and based on the pulse parameters, pulse determination engine 154 may generate energy values characterizing each of the pulses. For instance, pulse determination engine 154 may execute function 1 based on the corresponding pulse parameters to determine an energy value Y(t) at each peak location. Pulse determinator may then output the energy values for each of the pulses as pulse data 155. As an example, and assuming two peaks are detected for the first dimension location signal 151A, pulse determination engine 154 may output, for the first decoupled pulse, first pulse first dimension location 155A, and, for the second decoupled pulse, second pulse first dimension location 155D. Similarly, and assuming two peaks are detected for the second dimension location signal 151B, pulse determination engine 154 may output, for the first decoupled pulse, first pulse second dimension location 155B, and, for the second decoupled pulse, second pulse second dimension location 155E. Further, and assuming two peaks are detected for the energy signal 151C, pulse determination engine 154 may output, for the first decoupled pulse, first pulse energy value 155C, and, for the second decoupled pulse, second pulse energy value 155F.

In addition, as described herein, pulse determination engine 154 may generate first time data 159A based on corresponding time data 157 received from TDC 156. The first time data 159A generated by pulse determination engine 154 characterizes a corresponding time (e.g., timestamp) associated with each of the first pulse first dimension location 155A, first pulse second dimension location 155B, and first pulse energy value 155C. In addition, pulse determination engine 154 may generate second time data 159B characterizing a corresponding time (e.g., timestamp) associated with each of the second pulse first dimension location 155D, second pulse second dimension location 155E, and second pulse energy value 155F. For example, pulse determination engine 154 may determine the first time data 159A for the first pulse first dimension location 155A, first pulse second dimension location 155B, and first pulse energy value 155C based on corresponding time data 157 received from TDC 156. Further, pulse determination engine 154 may determine a time for each of the second pulse first dimension location 155D, second pulse second dimension location 155E, and second pulse energy value 155F based on the first time data 159A and corresponding time offset values characterized by peak location data 154B. As described herein, each time offset value indicates an offset (e.g., time offset, sample offset) from a previous pulse. For example, the time offset value corresponding to each of the second pulse first dimension location 155D, second pulse second dimension location 155E, and second pulse energy value 155F may characterize an offset from the first pulse first dimension location 155A, first pulse second dimension location 155B, and first pulse energy value 155C, respectively. Based on these corresponding time offset values, pulse determination engine 154 may generate second time data 159B characterizing a time for second pulse first dimension location 155D, second pulse second dimension location 155E, and second pulse energy value 155F.

FIG. 1B is illustrated and described above with respect to decoupling two pulses on each of three signals merely for ease of readability reasons. In other embodiments as contemplated herein, three, four, or more pulses may be detected and decoupled from any number of received signals, such as from any of first dimension location signal 151A, second dimension location signal 151B, and the energy signal 151C.

Figure 1C:
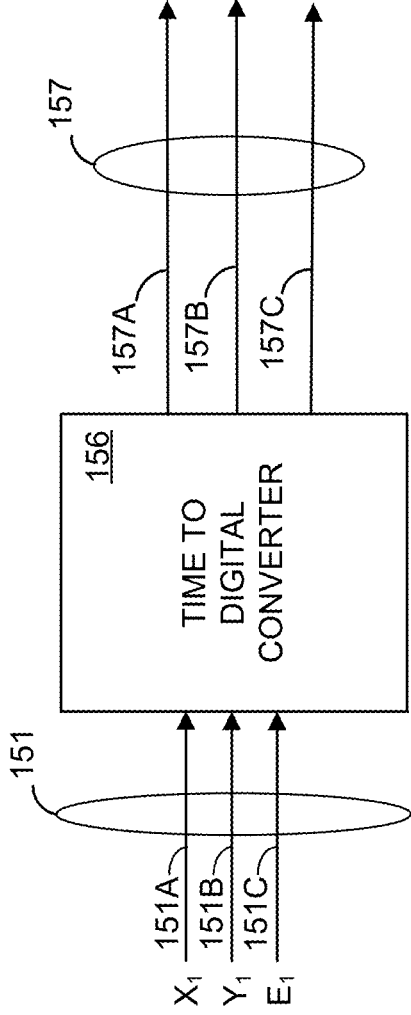

FIG. 1C illustrates an example of the TDC 156. In this example, TDC 156 receives first dimension location signal 151A, second dimension location signal 151B, and energy signal 151C from, for example, the scanner 150. In response to receiving each of the first dimension location signal 151A, second dimension location signal 151B, and energy signal 151C, the TDC 156 generates corresponding time data 157, namely, first dimension time data 157A, second dimension time data 157B, and energy time data 157C. In some instances, to generate the first dimension time data 157A, second dimension time data 157B, and energy time data 157C, TDC 156 may sample a system time (e.g., system time of the image scanning system 102).

FIG. 2 illustrates a computing device 200 that can be employed by any of the image scanning system 102 and the image reconstruction system 104. For instance, computing device 200 can implement one or more of the functions of the image scanning system 102 and/or image reconstruction system 104 described herein.

Computing device 200 can include one or more processors 201, working memory 202, one or more input-output devices 203, instruction memory 207, a transceiver 204, one or more communication ports 209, and a display 206, all operatively coupled to one or more data buses 208. Data buses 208 allow for communication among the various devices. Data buses 208 can include wired, or wireless, communication channels.

Processors 201 can include one or more distinct processors, each having one or more cores. Each of the distinct processors can have the same or different structure. Processors 201 can include one or more central processing units (CPUs), one or more graphics processing units (GPUs), application specific integrated circuits (ASICs), digital signal processors (DSPs), and the like.

Processors 201 can be configured to perform a certain function or operation by executing code, stored on instruction memory 207, embodying the function or operation. For example, processors 201 can be configured to perform one or more of the functions, methods, or operations disclosed herein.

Instruction memory 207 can be any memory device that can store instructions that can be accessed (e.g., read) and executed by processors 201. For example, instruction memory 207 can be a non-transitory, computer-readable storage medium such as a read-only memory (ROM), an electrically erasable programmable read-only memory (EE-PROM), flash memory, a removable disk, CD-ROM, any non-volatile memory, or any other suitable memory. For example, instruction memory 207 can store instructions that, when executed by one or more processors 201, cause one or more processors 201 to perform one or more of the functions of image reconstruction system 104, such as one or more of the histo-image generation processes, the multi-view attenuation histo-image generation processes, and/or the machine learning processes described herein.

Processors 201 can store data to, and read data from, working memory 202. For example, processors 201 can store a working set of instructions to working memory 202, such as instructions loaded from instruction memory 207. Processors 201 can also use working memory 202 to store dynamic data created during the operation of computing device 200. Working memory 202 can be a random access memory (RAM) such as a static random access memory (SRAM) or dynamic random access memory (DRAM), or any other suitable memory.

Input-output devices 203 can include any suitable device that allows for data input or output. For example, input-output devices 203 can include one or more of a keyboard, a touchpad, a mouse, a stylus, a touchscreen, a physical button, a speaker, a microphone, or any other suitable input or output device.

Communication port(s) 209 can include, for example, a serial port such as a universal asynchronous receiver/transmitter (UART) connection, a Universal Serial Bus (USB) connection, or any other suitable communication port or connection. In some examples, communication port(s) 209 allows for the programming of executable instructions in instruction memory 207. In some examples, communication port(s) 209 allow for the transfer (e.g., uploading or downloading) of data, such as PET measurement data 111 and/or attenuation maps 105.

Display 206 can display user interface 205. User interface 205 can enable user interaction with computing device 200. For example, user interface 205 can be a user interface for an application that allows for the viewing of final image volumes 191. In some examples, a user can interact with user interface 205 by engaging input-output devices 203. In some examples, display 206 can be a touchscreen, where user interface 205 is displayed on the touchscreen.

Transceiver 204 allows for communication with a network, such as a Wi-Fi network, an Ethernet network, a cellular network, or any other suitable communication network. For example, if operating in a cellular network, transceiver 204 is configured to allow communications with the cellular network. Processor(s) 201 is operable to receive data from, or send data to, a network via transceiver 204.

Figure 3:
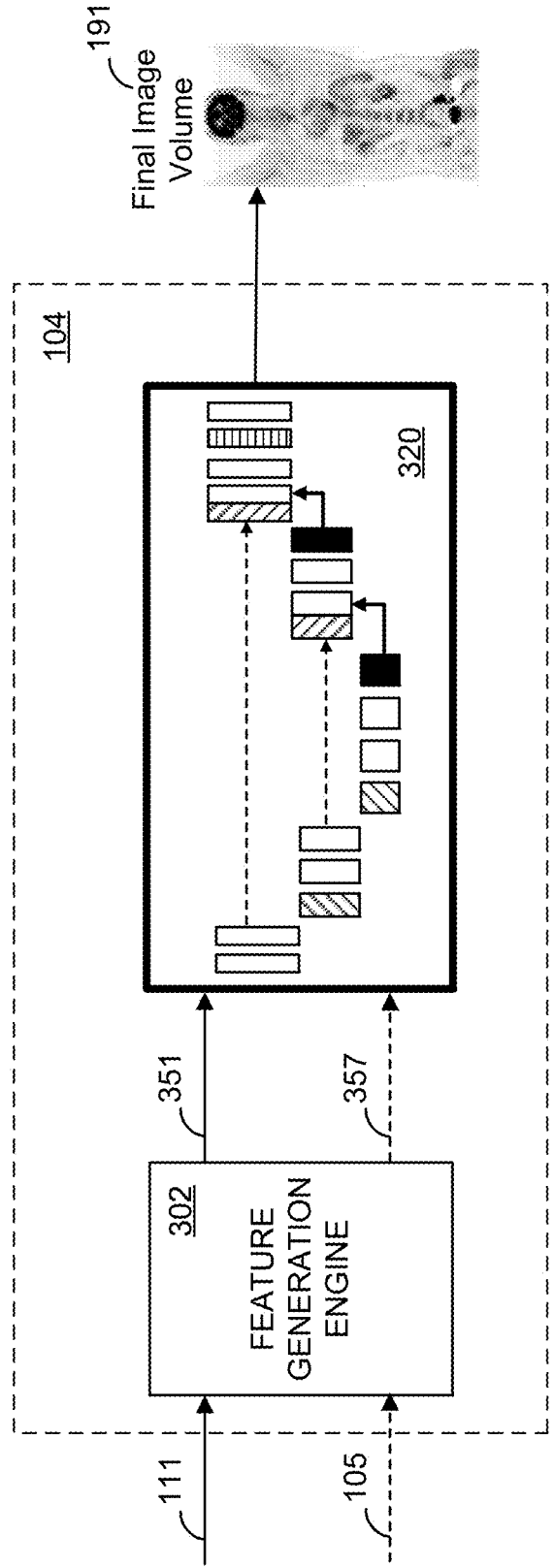
FIG. 3 illustrates a reconstruction of a nuclear image using a neural network, in accordance with some embodiments.

FIG. 3 illustrates exemplary portions of an image reconstruction system 104 that includes a feature generation engine 302 and a trained neural network 320. Image reconstruction system 104 may input the PET measurement data 111 to the feature generation engine 302. In response, feature generation engine 302 may generate detection features 351 based on the PET measurement data 111. Image reconstruction system 104 inputs the detection features 351 to the trained neural network 320. Based on the inputted detection features 351, the trained neural network 320 generates the final image volume 191.

In some examples, the feature generation engine 302 receives an attenuation map 105, and generates map features 357 based on the attenuation map 105. Image reconstruction system 104 may input the map features 357 to the trained neural network 320, and the trained neural network 320 may generate the final image volume 191 based on the inputted detection features 351 and map features 357.

Although the image reconstruction system 104 of FIG. 3 illustrates the generation of the final image volume 191 based on trained machine learning based processes, in other examples, image reconstruction system 104 may generate final image volumes 191 based on other processes, such as by applying analytical or iterative image reconstruction techniques to the PET measurement data 111 to generate the final image volume 191.

Figure 4:
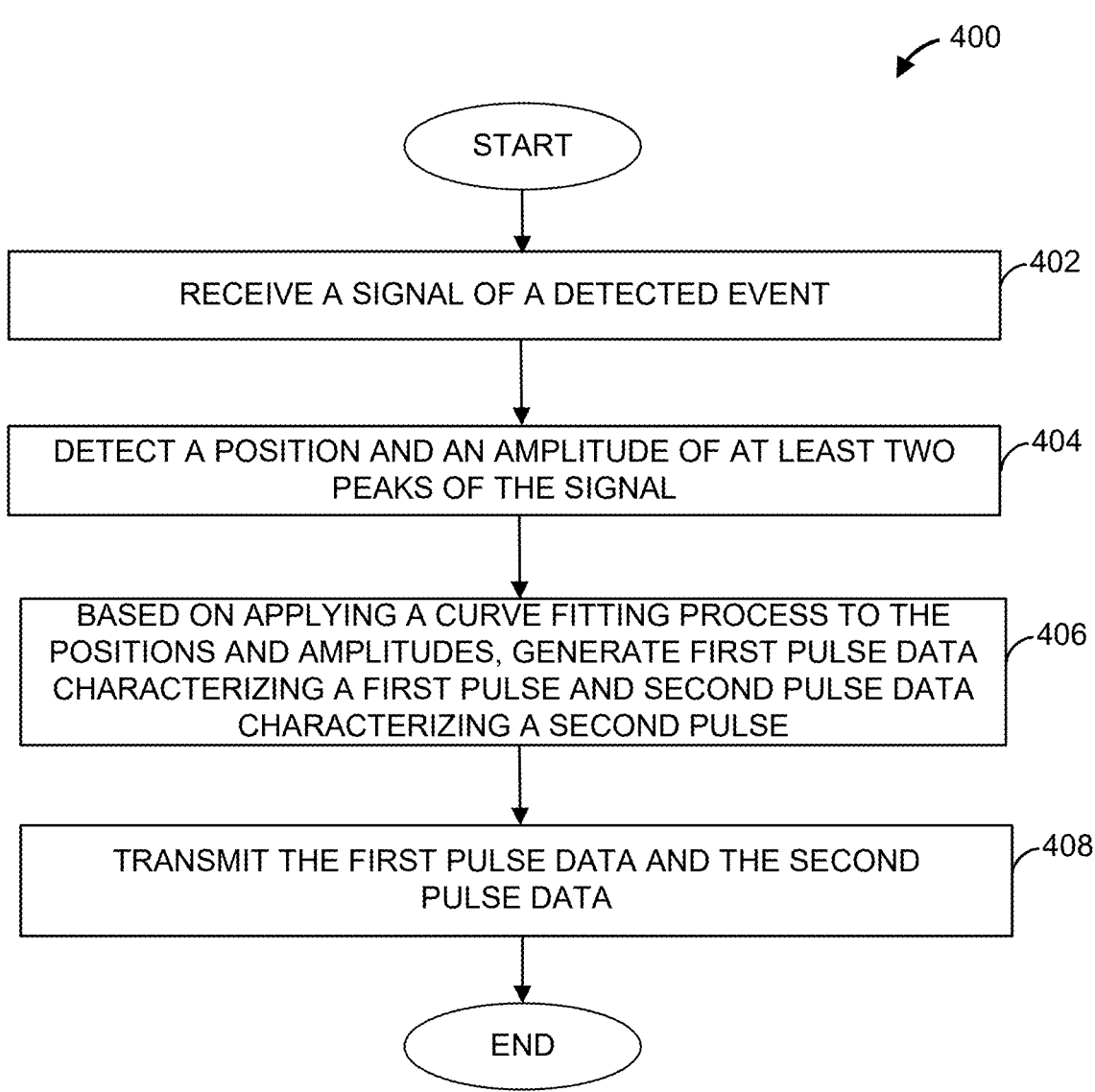
FIG. 4 is a flowchart of an example method to generate data characterizing multiple pulses, in accordance with some embodiments.

FIG. 4 is a flowchart of an example method 400 to generate data characterizing multiple pulses. The method can be performed by one or more computing devices, such as computing device 200, executing corresponding instructions.

Beginning at block 402, a signal of a detected event is received. For instance, as described herein, scanner 150 of the image scanning system 102 may scan a subject in its field-of-view, and may generate detection data 151 characterizing detection events. The detection data 151 may include, for a given crystal detection, an energy signal, a first location signal characterizing a first dimension location of the detection (e.g., X-axis location of the detecting crystal), and a second location signal characterizing a second dimension location of the detection (e.g., Y-axis location of the detecting crystal).

At block 404, a position and an amplitude of at least two peaks of the signal are detected. For instance, as described herein, computing device 200 may apply a peak detection process to the signal and, based on the application of the peak detection process, may detect a position (e.g., sample number) of each of the peaks of the signal. The detected positions may be estimated positions of possible peaks of the signal. Further, the computing device 200 may also determine an amplitude of each of the peaks based on their positions.

At block 406, a curve fitting process is applied to the positions and amplitudes. Based on the application of the curve fitting process, first pulse data characterizing a first pulse, and second pulse data characterizing a second pulse, is generated. For example, and as described herein, the curve fitting process may include inputting the peak locations and the peak amplitudes to an executed curve fitting model, such as one based on least square means. Based on the inputted peak locations and peak heights, the curve fitting process may include generating, by the executed curve fitting model, output data characterizing individual pulse parameters, such as values for Ks, Ki, tf, and tr for function 1 for each of the individual pulses. Further, and based on the individual pulse parameters for each pulse, the computing device 200 may determine an energy value for each pulse. For instance, the computing device 200 may execute Function 1 using the pulse parameters to determine one or more energy values, e.g., Y(t), for each corresponding pulse. The respective energy values characterize the first pulse and the second pulse.

Further, at block 408, the first pulse data and the second pulse data is transmitted. For example, the computing device 200 may transmit the first pulse data and the second pulse data to the image reconstruction system 104 to reconstruct an image.

FIG. 5 is a flowchart of an example method 500 to reconstruct an image based on timing correction data. The method can be performed by one or more computing devices, such as computing device 200, executing corresponding instructions.

Beginning at block 502, first location values and first amplitude values of at least two peaks of an energy signal, second location values and second amplitude values of at least two peaks of a first location signal, and third location values and third amplitude values of at least two peaks of a second location signal, are received. For example, computing device 200 may apply any of the peak detection process described herein to the energy signal 151C, the first dimension location signal 151A, and the second dimension location signal 151B to generate corresponding peak location values, and may determine corresponding amplitude values based on the peak location values.

At block 504, to decouple pulses of the energy signal, a curve fitting process is applied to the first location values and first position values and, based on the application of the curve fitting process, first energy pulse data charactering a first pulse, and second energy pulse data characterizing a second pulse, is generated. For example, computing device 200 may apply the curve fitting process to the peak location and amplitude values determined for energy signal 151C to generate first pulse energy value 155C and second pulse energy value 155F.

Further, at block 506, to decouple pulses of the first location signal, the curve fitting process is applied to the second location values and second position values and, based on the application of the curve fitting process, first location first pulse data charactering a first pulse, and first location second pulse data characterizing a second pulse, is generated. For example, computing device 200 may apply the curve fitting process to the peak location and amplitude values determined for the first dimension location signal 151A to generate first pulse first dimension location 155A and second pulse first dimension location 155D.

Proceeding to block 508, to decouple pulses of the second location signal, the curve fitting process is applied to the third location values and third position values and, based on the application of the curve fitting process, second location first pulse data charactering a first pulse, and second location second pulse data characterizing a second pulse, is generated. For example, computing device 200 may apply the curve fitting process to the peak location and amplitude values determined for the second dimension location signal 151B to generate first pulse second dimension location 155B and second pulse second dimension location 155E.

At block 510, a first pulse time offset value is determined based on the first position values, a second pulse time offset value is determined based on the second position values, and a third pulse time offset value is determined based on the third position values. The pulse time offset values characterize a time between corresponding pulses. For example, and as described herein, computing device 200 may determine each of the pulse time offset values based on a difference between the corresponding position values.

Further, and at block 512, the first energy pulse data, the second energy pulse data, the first location first pulse data, the second location first pulse data, the first location second pulse data, the second location second pulse data, the first pulse time offset value, the second pulse time offset value, and the third pulse time offset value is transmitted. For example, this data may be transmitted to TDC 156 to determine times for each of the decoupled pulses, as described herein.

The following is a list of non-limiting illustrative embodiments disclosed herein:

Illustrative Embodiment 1: A computer-implemented method comprising:

receiving at least one signal characterizing a detection event;

applying a peak detection process to the at least one signal and, based on the application of the peak detection process, detecting a position of each of at least two peaks of the at least one signal;

determining an amplitude of each of the at least two peaks of the at least one signal;

applying a curve fitting process to the position and the amplitude of each of the at least two peaks and, based on the application of the curve fitting process, determining an energy value for each of the at least two peaks; and transmitting the energy value for each of the at least two peaks.

Illustrative Embodiment 2: The computer-implemented method of illustrative embodiment 1, wherein applying the curve fitting process comprises:

inputting the position and the amplitude of a first peak of the at least two peaks to an executed curve fitting model;

receiving parameter values from the executed curve fitting model; and determining the energy value for the first peak based on the parameter values.

Illustrative Embodiment 3: The computer-implemented method of illustrative embodiment 2, wherein the executed curve fitting model is based on a least squares means algorithm.

Illustrative Embodiment 4: The computer-implemented method of any of illustrative embodiments 2-3, wherein applying the curve fitting process comprises:

inputting the position and the amplitude of a second peak of the at least two peaks to the executed curve fitting model;

receiving additional parameter values from the executed curve fitting model; and determining the energy value for the second peak based on the additional parameter values.

Illustrative Embodiment 5: The computer-implemented method of any of illustrative embodiments 1-4, wherein the at least two peaks consists of two peaks.

Illustrative Embodiment 6: The computer-implemented method of any of illustrative embodiments 1-5, further comprising generating a time for each of the at least two peaks based on the respective position of each of the at least two peaks.

Illustrative Embodiment 7: The computer-implemented method of illustrative embodiment 6, wherein generating the time for each of the at least two peaks:

generating a first time for a first of the at least two peaks based on sampling a system time;

determining an offset value between the at least two peaks based on the position of each of the at least two peaks; and generating a second time for a second of the at least two peaks based on the first time and the offset value.

Illustrative Embodiment 8: The computer-implemented method of any of illustrative embodiments 1-7, further comprising receiving the at least one signal from a scanner of an image scanning system.

Illustrative Embodiment 9: The computer-implemented method of any of illustrative embodiments 1-8, wherein the at least one signal comprises a first signal that characterizes energy levels of the detection event.

Illustrative Embodiment 10: The computer-implemented method of illustrative embodiment 9, wherein the at least one signal comprises a second signal that characterizes a first dimension location of a crystal that detected the detection event.

Illustrative Embodiment 11: The computer-implemented method of illustrative embodiment 10, wherein the at least one signal comprises a third signal that characterizes a second dimension location of the crystal that detected the detection event.

Illustrative Embodiment 12: The computer-implemented method of any of illustrative embodiments 1-11, further comprising generating image measurement data based on the energy value for each of the at least two peaks.

Illustrative Embodiment 13: The computer-implemented method of illustrative embodiment 12, wherein the image measurement data is positron emission tomography (PET) measurement data.

Illustrative Embodiment 14: The computer-implemented method of any of illustrative embodiments 1-13, wherein applying the curve fitting process comprises:

generating output data characterizing at least two pulses; determining an area under each of the at least two pulses; and determining the energy value for each of the at least two peaks based on the respective area.

Illustrative Embodiment 15: A non-transitory computer readable medium storing instructions that, when executed by at least one processor, cause the at least one processor to perform operations comprising:

receiving at least one signal characterizing a detection event;

applying a peak detection process to the at least one signal and, based on the application of the peak detection process, detecting a position of each of at least two peaks of the at least one signal;

determining an amplitude of each of the at least two peaks of the at least one signal;

applying a curve fitting process to the position and the amplitude of each of the at least two peaks and, based on the application of the curve fitting process, determining an energy value for each of the at least two peaks; and transmitting the energy value for each of the at least two peaks.

Illustrative Embodiment 16: The non-transitory computer readable medium of claim 15 wherein the instructions, when executed by the at least one processor, further cause the at least one processor to perform operations comprising:

inputting the position and the amplitude of a first peak of the at least two peaks to an executed curve fitting model;

receiving parameter values from the executed curve fitting model; and

determining the energy value for the first peak based on the parameter values.

Illustrative Embodiment 17: The non-transitory computer readable medium of claim 16, wherein the executed curve fitting model is based on a least squares means algorithm.

Illustrative Embodiment 18: The non-transitory computer readable medium of any of illustrative embodiments 16-17, wherein the instructions, when executed by the at least one processor, further cause the at least one processor to perform operations comprising:

inputting the position and the amplitude of a second peak of the at least two peaks to the executed curve fitting model;

receiving additional parameter values from the executed curve fitting model; and determining the energy value for the second peak based on the additional parameter values.

Illustrative Embodiment 19: The non-transitory computer readable medium of any of illustrative embodiments 15-18, wherein the at least two peaks consists of two peaks.

Illustrative Embodiment 20: The non-transitory computer readable medium of any of illustrative embodiments 14-19, wherein the instructions, when executed by the at least one processor, further cause the at least one processor to perform operations comprising generating a time for each of the at least two peaks based on the respective position of each of the at least two peaks.

Illustrative Embodiment 21: The non-transitory computer readable medium of illustrative embodiment 20, wherein the instructions, when executed by the at least one processor, further cause the at least one processor to perform operations comprising:

generating a first time for a first of the at least two peaks based on sampling a system time;

determining an offset value between the at least two peaks based on the position of each of the at least two peaks; and generating a second time for a second of the at least two peaks based on the first time and the offset value.

Illustrative Embodiment 22: The non-transitory computer readable medium of any of illustrative embodiments 15-21, wherein the instructions, when executed by the at least one processor, further cause the at least one processor to perform operations comprising receiving the at least one signal from a scanner of an image scanning system.

Illustrative Embodiment 23: The non-transitory computer readable medium of any of illustrative embodiments 15-22, wherein the at least one signal comprises a first signal that characterizes energy levels of the detection event.

Illustrative Embodiment 24: The non-transitory computer readable medium of illustrative embodiment 23, wherein the at least one signal comprises a second signal that characterizes a first dimension location of a crystal that detected the detection event.

Illustrative Embodiment 25: The non-transitory computer readable medium of illustrative embodiment 24, wherein the at least one signal comprises a third signal that characterizes a second dimension location of the crystal that detected the detection event.

Illustrative Embodiment 26: The non-transitory computer readable medium of any of illustrative embodiments 15-25, wherein the instructions, when executed by the at least one processor, further cause the at least one processor to perform operations comprising generating image measurement data based on the energy value for each of the at least two peaks.

Illustrative Embodiment 27: The non-transitory computer readable medium of illustrative embodiment 16, wherein the image measurement data is positron emission tomography (PET) measurement data.

Illustrative Embodiment 28: The non-transitory computer readable medium of any of illustrative embodiments 15-27, wherein the instructions, when executed by the at least one processor, further cause the at least one processor to perform operations comprising:

generating output data characterizing at least two pulses;

determining an area under each of the at least two pulses; and determining the energy value for each of the at least two peaks based on the respective area.

Illustrative Embodiment 29: A system comprising:

a memory device storing instructions;

a transceiver; and at least one processor communicatively coupled to the transceiver and to the memory device, the at least one processor configured to execute the instructions to:

receive, via the transceiver, at least one signal characterizing a detection event;

apply a peak detection process to the at least one signal and, based on the application of the peak detection process, detect a position of each of at least two peaks of the at least one signal;

determine an amplitude of each of the at least two peaks of the at least one signal;

apply a curve fitting process to the position and the amplitude of each of the at least two peaks and, based on the application of the curve fitting process, determine an energy value for each of the at least two peaks; and transmit, via the transceiver, the energy value for each of the at least two peaks.

Illustrative Embodiment 30: The system of illustrative embodiment 29, wherein the at least one processor is configured to execute the instructions to:

input the position and the amplitude of a first peak of the at least two peaks to an executed curve fitting model;

receive parameter values from the executed curve fitting model; and determine the energy value for the first peak based on the parameter values.

Illustrative Embodiment 31: The system of illustrative embodiment 30, wherein the executed curve fitting model is based on a least squares means algorithm.

Illustrative Embodiment 32: The system of any of illustrative embodiments 30-31, wherein the at least one processor is configured to execute the instructions to:

input the position and the amplitude of a second peak of the at least two peaks to the executed curve fitting model;

receive additional parameter values from the executed curve fitting model; and determine the energy value for the second peak based on the additional parameter values.

Illustrative Embodiment 33: The system of any of illustrative embodiments 29-32, wherein the at least two peaks consists of two peaks.

Illustrative Embodiment 34: The system of any of illustrative embodiments 29-33, wherein the at least one processor is configured to execute the instructions to generate a time for each of the at least two peaks based on the respective position of each of the at least two peaks.

Illustrative Embodiment 35: The system of illustrative embodiment 34, wherein the at least one processor is configured to execute the instructions to:

generate a first time for a first of the at least two peaks based on sampling a system time;

determine an offset value between the at least two peaks based on the position of each of the at least two peaks; and generate a second time for a second of the at least two peaks based on the first time and the offset value.

Illustrative Embodiment 36: The system of any of illustrative embodiments 29-35, wherein the at least one processor is configured to execute the instructions to receive the at least one signal from a scanner of an image scanning system.

Illustrative Embodiment 37: The system of any of illustrative embodiments 29-36, wherein the at least one signal comprises a first signal that characterizes energy levels of the detection event.

Illustrative Embodiment 38: The system of illustrative embodiment 37, wherein the at least one signal comprises a second signal that characterizes a first dimension location of a crystal that detected the detection event.

Illustrative Embodiment 39: The system of illustrative embodiment 38, wherein the at least one signal comprises a third signal that characterizes a second dimension location of the crystal that detected the detection event.

Illustrative Embodiment 40: The system of any of illustrative embodiments 29-39, wherein the at least one processor is configured to execute the instructions to generate image measurement data based on the energy value for each of the at least two peaks.

Illustrative Embodiment 41: The system of illustrative embodiment 40, wherein the image measurement data is positron emission tomography (PET) measurement data.

Illustrative Embodiment 42: The system of any of illustrative embodiments 29-41, wherein the at least one processor is configured to execute the instructions to:

generate output data characterizing at least two pulses;

determine an area under each of the at least two pulses; and determine the energy value for each of the at least two peaks based on the respective area.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein can be applied to other embodiments without the use of inventive faculty. The present disclosure is not intended to be limited to the embodiments shown herein, but is to be accorded the widest scope consistent with the principles and novel features disclosed herein.

What is claimed is:

1. A computer-implemented method comprising:

receiving at least one signal characterizing a detection event;

applying a peak detection process to the at least one signal and, based on the application of the peak detection process, detecting a position of each of at least two peaks of the at least one signal;

determining an amplitude of each of the at least two peaks of the at least one signal;

applying a curve fitting process to the position and the amplitude of each of the at least two peaks and, based on the application of the curve fitting process, determining an energy value for each of the at least two peaks; and transmitting the energy value for each of the at least two peaks.

2. The computer-implemented method of claim 1, wherein applying the curve fitting process comprises:

inputting the position and the amplitude of a first peak of the at least two peaks to an executed curve fitting model;

receiving parameter values from the executed curve fitting model; and determining the energy value for the first peak based on the parameter values.

3. The computer-implemented method of claim 2, wherein the executed curve fitting model is based on a least squares means algorithm.

4. The computer-implemented method of claim 2, wherein applying the curve fitting process comprises:

inputting the position and the amplitude of a second peak of the at least two peaks to the executed curve fitting model;

receiving additional parameter values from the executed curve fitting model; and determining the energy value for the second peak based on the additional parameter values.

5. The computer-implemented method of claim 1, wherein the at least two peaks consists of two peaks.

6. The computer-implemented method of claim 1, further comprising generating a time for each of the at least two peaks based on the respective position of each of the at least two peaks.

7. The computer-implemented method of claim 6, wherein generating the time for each of the at least two peaks:

generating a first time for a first of the at least two peaks based on sampling a system time;

determining an offset value between the at least two peaks based on the position of each of the at least two peaks; and generating a second time for a second of the at least two peaks based on the first time and the offset value.

8. The computer-implemented method of claim 1, further comprising receiving the at least one signal from a scanner of an image scanning system.

9. The computer-implemented method of claim 1, wherein the at least one signal comprises a first signal that characterizes energy levels of the detection event.

10. The computer-implemented method of claim 9, wherein the at least one signal comprises a second signal that characterizes a first dimension location of a crystal that detected the detection event.

11. The computer-implemented method of claim 10, wherein the at least one signal comprises a third signal that characterizes a second dimension location of the crystal that detected the detection event.

12. The computer-implemented method of claim 1, further comprising generating image measurement data based on the energy value for each of the at least two peaks.

13. The computer-implemented method of claim 12, wherein the image measurement data is positron emission tomography (PET) measurement data.

14. The computer-implemented method of claim 1, wherein applying the curve fitting process comprises:

generating output data characterizing at least two pulses;

determining an area under each of the at least two pulses; and determining the energy value for each of the at least two peaks based on the respective area.

15. A non-transitory computer readable medium storing instructions that, when executed by at least one processor, cause the at least one processor to perform operations comprising:

receiving at least one signal characterizing a detection event;

applying a peak detection process to the at least one signal and, based on the application of the peak detection process, detecting a position of each of at least two peaks of the at least one signal;

determining an amplitude of each of the at least two peaks of the at least one signal;

applying a curve fitting process to the position and the amplitude of each of the at least two peaks and, based on the application of the curve fitting process, determining an energy value for each of the at least two peaks; and transmitting the energy value for each of the at least two peaks.

16. The non-transitory computer readable medium of claim 15 wherein the instructions, when executed by the at least one processor, further cause the at least one processor to perform operations comprising:

inputting the position and the amplitude of a first peak of the at least two peaks to an executed curve fitting model;

receiving parameter values from the executed curve fitting model; and determining the energy value for the first peak based on the parameter values.

17. The non-transitory computer readable medium of claim 15, wherein the instructions, when executed by the at least one processor, further cause the at least one processor to perform operations comprising generating a time for each of the at least two peaks based on the respective position of each of the at least two peaks.

18. The non-transitory computer readable medium of claim 17, wherein the instructions, when executed by the at least one processor, further cause the at least one processor to perform operations comprising:

generating a first time for a first of the at least two peaks based on sampling a system time;

determining an offset value between the at least two peaks based on the position of each of the at least two peaks; and generating a second time for a second of the at least two peaks based on the first time and the offset value.

19. A system comprising:

a memory device storing instructions;

a transceiver; and at least one processor communicatively coupled to the transceiver and to the memory device, the at least one processor configured to execute the instructions to:

receive, via the transceiver, at least one signal characterizing a detection event;

apply a peak detection process to the at least one signal and, based on the application of the peak detection process, detect a position of each of at least two peaks of the at least one signal;

determine an amplitude of each of the at least two peaks of the at least one signal;

apply a curve fitting process to the position and the amplitude of each of the at least two peaks and, based on the application of the curve fitting process, determine an energy value for each of the at least two peaks; and transmit, via the transceiver, the energy value for each of the at least two peaks.

20. The system of claim 19, wherein the at least one processor is configured to execute the instructions to:

input the position and the amplitude of a first peak of the at least two peaks to an executed curve fitting model;

receive parameter values from the executed curve fitting model; and determine the energy value for the first peak based on the parameter values.

\* \* \* \* \*